(12) United States Patent
Boyd et al.

(10) Patent No.: US 10,175,200 B2
(45) Date of Patent: Jan. 8, 2019

(54) METHODS AND SYSTEMS FOR DETECTING NONUNIFORMITIES IN A MATERIAL, COMPONENT, OR STRUCTURE

(71) Applicant: Prime Photonics, LC, Blacksburg, VA (US)

(72) Inventors: Clark Davis Boyd, Portsmouth, VA (US); David Todd Gray, Blacksburg, VA (US); Jonathan Drapala Sides, Leonardtown, MD (US)

(73) Assignee: Prime Photonics, LC, Blacksburg, VA (US)

( * ) Notice: Subject to any disclaimer, the term of this patent is extended or adjusted under 35 U.S.C. 154(b) by 95 days.

(21) Appl. No.: 14/718,522

(22) Filed: May 21, 2015

(65) Prior Publication Data
US 2015/0346153 A1 Dec. 3, 2015

Related U.S. Application Data

(60) Provisional application No. 62/004,985, filed on May 30, 2014.

(51) Int. Cl.
*G01N 27/82* (2006.01)
*G01N 1/28* (2006.01)

(52) U.S. Cl.
CPC ............ *G01N 27/82* (2013.01); *G01N 1/28* (2013.01)

(58) Field of Classification Search
None
See application file for complete search history.

(56) References Cited

U.S. PATENT DOCUMENTS

| | | | |
|---|---|---|---|
| 4,184,374 A | 1/1980 | Thompson et al. | |
| 4,312,231 A | 1/1982 | Kawashima et al. | |
| 4,523,473 A | 6/1985 | Chamuel | |
| 4,769,598 A | 9/1988 | Krieg et al. | |
| 4,793,185 A | 12/1988 | Boettger et al. | |
| 5,481,916 A | 1/1996 | Macecek et al. | |
| 6,529,029 B1 * | 3/2003 | Bruce | G01R 31/303 324/301 |
| 7,385,392 B2 * | 6/2008 | Schlicker | G01N 27/82 324/242 |

(Continued)

FOREIGN PATENT DOCUMENTS

| | | |
|---|---|---|
| CN | 101706476 B | 6/2011 |
| CN | 102798666 A | 11/2012 |

(Continued)

OTHER PUBLICATIONS

Dave Van Ess, "Synchronous Detection Plays A Role in Better Analog Design", Sep 30, 2009, Electronic Design, http://www.electronicdesign.com/analog/synchronous-detection-plays-role-better-analog-design.

*Primary Examiner* — Jermele M Hollington
*Assistant Examiner* — Douglas X Rodriguez
(74) *Attorney, Agent, or Firm* — New River Valley IP Law, P.C.; Michele L. Mayberry; Timothy D. Nolan (57) ABSTRACT

Methods of detecting non-uniformities in a material are described. Such methods can comprise inducing changes in strain state or changing the magnetic moment of a material and measuring magnetic flux leakage that is synchronous with the changes in strain state or magnetic moment, while simultaneously applying an external magnetic field to control the relative magnitude of the magnetic flux leakage.

35 Claims, 6 Drawing Sheets

(56) References Cited

U.S. PATENT DOCUMENTS

| | | | | |
|---|---|---|---|---|
| 8,146,431 B2* | 4/2012 | Yashan | ............... | G01N 27/87 73/597 |
| 2011/0000338 A1* | 1/2011 | Koshihara | ............ | G01N 27/83 75/392 |
| 2014/0368191 A1* | 12/2014 | Goroshevskiy | ........ | G01N 27/85 324/201 |

FOREIGN PATENT DOCUMENTS

| | | |
|---|---|---|
| CN | 202814925 U | 3/2013 |
| CN | 202854097 U | 4/2013 |
| CN | 103353478 A | 10/2013 |
| FR | 2547056 | 12/1984 |
| GB | 2113392 | 8/1983 |
| JP | S5767852 | 4/1982 |
| JP | S60149964 | 8/1985 |
| JP | S60164249 | 8/1985 |
| JP | S62191758 | 8/1987 |
| JP | H0926417 | 1/1997 |
| JP | 2002090349 | 3/2002 |
| JP | 2002310997 | 10/2002 |
| JP | 2005214686 | 8/2005 |
| JP | 2006329868 | 12/2006 |
| JP | 2008232666 | 10/2008 |

* cited by examiner

METHODS AND SYSTEMS FOR DETECTING NONUNIFORMITIES IN A MATERIAL, COMPONENT, OR STRUCTURE

CROSS-REFERENCE TO RELATED APPLICATIONS

The present application relies on the disclosure of and claims priority to and the benefit of the filing date of U.S. Provisional Application No. 62/004,985, filed May 30, 2014, the disclosure of which is hereby incorporated by reference herein in its entirety.

BACKGROUND OF THE INVENTION

Field of the Invention

The present disclosure relates to non-destructive testing of materials, components, or structures for nonuniformities such as flaws, defects, and cracks. More particularly, embodiments of the present disclosure relate to methods and systems for non-destructive testing through measurement of magnetic flux leakage that is synchronous with induced changes in strain state in the material in the presence of an applied magnetic field.

Description of Related Art

Non-Destructive Testing (NDT) technologies, as the name implies, involves testing of materials for discontinuities and other defects in a way that does not damage the materials or otherwise impact their future usefulness. A number of conventional technologies can be used for NDT (also referred to as Nondestructive Examination (NDE), Nondestructive Inspection (NDI), and Nondestructive Evaluation (NDE)) including magnetic particle, liquid penetrant, radiography, ultrasonic testing, and eddy current, to name a few. Magnetic particle testing is useful for detecting surface and slightly subsurface discontinuities in ferromagnetic materials. Similarly, liquid penetrant testing can detect material defects open to the surface or to detect open surface cracks. However, neither of these technologies is capable of measuring subsurface flaws.

Eddy current testing is a more sophisticated method of detecting surface flaws. When an AC current flows in a coil in close proximity to a conducting surface the magnetic field of the coil will induce circulating (eddy) currents in that surface. The magnitude and phase of the eddy currents will affect the loading on the coil and thus its impedance. This change in impedance can be measured, and used to determine the existence of a surface flaw. An Arrayed Eddy Current System is an adaptation of the basic eddy current measurement system. Placing a drive current and receiver coils on a flexible structure and rastering over a surface, a 2-D image of the surface can be determined. Certain companies have refined this approach to provide a very high probability of detection for surface flaws. The primary drawback is that this technology cannot directly measure the depth of the flaw.

Radiography and ultrasonic testing can be used to detect subsurface flaws. Radiography testing involves placing the material to be tested between a radiation source and a film or detector. Flaws in the material will result in differences in absorption recorded on the film or detector. Imaging techniques such as Computed Tomography (CT), Digital Radiography and Computed Radiography (CR) are replacing conventional film radiography in industrial radiographic testing. In ultrasonic testing, high frequency sound waves are transmitted through an object through a transducer, and cracks or other discontinuities will return reflected waves back to the transducer. However, defects identified by these methods may still be difficult to locate, or these methods may miss small defects entirely. Current NDE techniques are inadequate for detecting defects that are less than 100 um or that are located more than a few tens of microns below the surface. This is because such technologies use ultrasonic methods (good penetration—poor resolution) or eddy current methods (poor penetration—medium resolution) independently.

Emerging NDT technologies for detecting subsurface defects include thermal imaging, SQUID eddy current, and Synchrotron X-Ray diffraction. Thermal imaging can detect shallow subsurface defects, but it suffers from poor accuracy and resolution. SQUID Eddy Current techniques use an extremely sensitive magnetometer to detect subsurface flaws, but it needs to be kept at cryogenic temperatures, relegating it laboratory use only. Synchrotron X-Ray diffraction can be used to detect flaws through measurement of residual stress in a material, but this technique requires a particle accelerator and thus is not portable or usually practical. Thus, there is a need in the art for more sensitive, accurate, and practical NDT technologies capable of detecting both surface and subsurface defects.

SUMMARY OF THE INVENTION

The present disclosure provides a method for detecting a nonuniformity or other defect in a material, component, or structure comprising applying ultrasonic energy along with a magnetic bias (either uniform or with a spatial gradient and either constant with time or time variant) to a specimen under test. Perturbations caused by surface or internal defects can be enhanced to improve characterization of these defects. If the test item is defect-free, the flux leakage through the surface will be relatively uniform. Not wishing to be bound by a particular theory, ultrasonic energy impinging upon the defect, may cause cyclic dimensional, magnetic, and/or eddy current effects that can be detected with high resolution near the surface.

In one embodiment, the present disclosure provides a method of detecting a nonuniformity in a material, component, or structure, the method comprising inducing changes in strain state in the material and measuring magnetic flux leakage that is synchronous with the changes in strain state.

In another embodiment, the present disclosure provides a method of detecting a nonuniformity in a material, component, or structure, the method comprising changing the magnetic moment of the material through the Villari effect and measuring magnetic flux leakage that is synchronous with changes in the magnetic moment.

In another embodiment, the present disclosure provides a method of detecting a nonuniformity in a material, component, or structure, the method comprising applying periodic mechanical force to the material in a manner sufficient to induce changes in strain state in the material, and measuring magnetic flux leakage that is synchronous with the changes in strain state.

In another embodiment, the present disclosure provides a method of detecting a nonuniformity in a material, component, or structure, the method comprising exciting the material with periodic waves of ultrasonic energy in a manner sufficient to induce cycles of compression and tension in the material, and measuring magnetic flux leakage that is synchronous with the cycles of compression and tension.

In another embodiment, the present disclosure provides a method of detecting a nonuniformity in a material, component, or structure, the method comprising the simultaneous steps of applying an external magnetic field to the material; inducing periodic changes in strain state in the material; and measuring magnetic flux leakage that is synchronous with the changes in strain state.

In another embodiment, the present disclosure provides a method of detecting a nonuniformity in a material, component, or structure, the method comprising the simultaneous steps of applying an external magnetic field to the material, applying periodic mechanical force to the material in a manner sufficient to induce changes in strain state in the material, and measuring magnetic flux leakage that is synchronous with the changes in strain state.

In another embodiment, the present disclosure provides a method of detecting a nonuniformity in a material, component, or structure, the method comprising the optionally simultaneous steps of applying an external magnetic field to the material, exciting the material with periodic waves of ultrasonic energy in a manner sufficient to induce cycles of compression and tension in the material, and measuring magnetic flux leakage that is synchronous with the cycles of compression and tension. Preferably, one or more or all of these steps are performed simultaneously.

In another embodiment, the present disclosure provides a method of detecting a nonuniformity in a material, component, or structure, the method comprising the optionally simultaneous steps of applying an external magnetic field to the material, inducing a cycle of tension and compression in the material, and measuring magnetic flux leakage that is synchronous with the cycles of compression and tension. Preferably, one or more or all of these steps are performed simultaneously.

In any embodiment of this disclosure, the magnetic flux leakage may be measured by capturing a first scan of the material when the material is in compression, capturing a second scan of the material when the material is in tension, and differentiating the first and second scans. In the context of this disclose, when referring to differentiating, such as differentiating or the differentiation of two or more scans, it is not critical which scan is differentiated from the other and differentiating the first scan from the second scan is meant to be interchangeable with differentiating the second scan from the first scan.

In any embodiment of this disclosure, the magnetic flux leakage may be measured by capturing a first scan of the material when the material is in tension, capturing a second scan of the material when the material is in compression, and differentiating the first and second scans.

In any embodiment of this disclosure, the first scan and second scan may be obtained from a single vector magnetometer that is rasterized in space.

In any embodiment of this disclosure, the first scan and second scan may be obtained from an array of magnetometers.

In any embodiment of this disclosure, the changes in strain state may be a mechanically-induced non-uniform strain.

In any embodiment of this disclosure, the magnitude of the flux leakage may be modulated through use of an exterior magnetic bias field.

In any embodiment of this disclosure, the magnitude of the flux leakage may be modulated through the use of a DC bias.

In any embodiment of this disclosure, the changes in strain state may be induced at a cycle of tension and compression.

In any embodiment, the magnetic flux leakage may be measured by a single vector magnetometer that is rasterized in space to characterize a full magnetic gradient tensor resulting from mechanically-induced changes in strain state.

In any embodiment of this disclosure, the magnetic flux leakage may be measured through multiple magnetic sensors configured into a magnetic gradiometer that is rastered to characterize a full magnetic gradient tensor resulting from mechanically-induced changes in strain state.

In any embodiment of this disclosure, the magnetic flux leakage is measured through multiple magnetic sensors configured to characterize a full magnetic gradient tensor with no sensor motion relative to the material under test.

In any embodiment of this disclosure, the nonuniformity may be a surface crack, strain, or corrosion; subsurface crack, strain, or corrosion; occluded crack, strain, or corrosion; dissimilar material joint; coating; alloy precipitate, inclusion, or slag; or any combination thereof.

In any embodiment of this disclosure, the flux leakage may result from magnetostriction of materials resulting in changes in magnetic moment.

In any embodiment of this disclosure, the flux leakage may result from strain concentration resulting in increased localized heating that changes permeability, susceptibility, or saturation magnetization.

In any embodiment of this disclosure, the flux leakage may result from physical changes in defects that alter internal demagnetization fields to effect changes in permeability or vector of magnetic moment.

In any embodiment of this disclosure, the flux leakage may result from changes in magnetic reluctance that allow for alterations in flux leakage paths.

In any embodiment, a first scan of the material is captured when the material is in tension and a second scan of the material is captured when the material is in compression and the first and second scans are differentiated.

In any embodiment of this disclosure, a first scan of the material is captured when the material is in compression and a second scan of the material is captured when the material is in tension and the first scan is differentiated from the second scan.

In any embodiment of this disclosure, $$\left.\frac{\partial H_x}{\partial x}\right|_{comp-} - \left.\frac{\partial H_x}{\partial x}\right|_{tens=} \Delta \frac{\partial H_x}{\partial x}.$$

In any embodiment of this disclosure, multiple scans are performed at different x, y and z coordinates to create a 3-dimensional (3D) image. In embodiments, a Fourier transformation may be used to create a 3D image.

In any embodiment of this disclosure, the exterior magnetic bias field is induced by a Helmholtz coil.

In any embodiment of this disclosure, application of ultrasonic energy produces the mechanically-induced non-uniform strain. In embodiments, ultrasonic Rayleigh waves are applied to produce the mechanically-induced non-uniform strain. In embodiments, ultrasonic Lamb waves are applied to produce the mechanically-induced non-uniform strain.

In any embodiment of this disclosure, the magnetic sensor may be based on nitrogen vacancies in diamond.

In embodiments, the material may be a ferrous or a non-ferrous material.

In any embodiment of this disclosure, the material may be a solid material.

In any embodiment of this disclosure, the material may be configured as a component or structure. As used in this disclosure, the terms material, component, and structure may be used interchangeably and refer to any object for which a nondestructive evaluation is desired.

In any embodiment of this disclosure, a uniform magnetic bias is applied.

In any embodiment of this disclosure, a magnetic bias with a spatial gradient is applied.

In embodiments, the magnetic bias is constant with time.

In any embodiment of this disclosure, the magnetic bias is time variant.

In embodiments, the present disclosure provides a system for detecting a nonuniformity in a material, component, or structure, the system comprising an ultrasound source, one or more magnetometers, and a magnetic field source, wherein the ultrasound source is configured to induce a cycle of compression and tension in a test sample and the one or more magnetometers are configured to scan the test sample when it is in compression and when it is in tension; wherein the magnetic field source is configured to control the relative magnitude of any flux leakage in the test sample.

In any embodiment of this disclosure, the ultrasound source may comprise an electronic transducer. In embodiments, the electronic transducer may comprise a piezoelectric material.

In any embodiment of this disclosure, the magnetic field source may comprise a Helmholtz coil. In embodiments, the system may comprise a single vector magnetometer or an array of magnetometers.

In any embodiment of this disclosure, the system may comprise an imaging device configured for displaying an image of the test sample.

In any embodiment of this disclosure, the system may comprise a processor and a set of computer-executable instructions configured to obtain a 3D image of the test sample from multiple scans by the one or more magnetometers.

These embodiments and additional embodiments and their advantages and usefulness will be further set forth in the foregoing drawings and detailed description of the invention.

BRIEF DESCRIPTION OF THE DRAWINGS

The accompanying drawings illustrate certain aspects of embodiments of the present invention, and should not be used to limit the invention. Together with the written description the drawings serve to explain certain principles of the invention.

FIGS. 6A-6D are schematic diagrams showing synchronous detection of an internal flaw with magnetic background noise, where

DETAILED DESCRIPTION OF VARIOUS EMBODIMENTS OF THE INVENTION

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

Embodiments of the present disclosure provide methods for the detection of nonuniformities within a test sample of a material, component, or structure, through synchronous detection of modulated magnetic flux leakage.

In embodiments, the relative magnitude of the flux leakage can be controlled through use of an exterior magnetic bias field.

In embodiments, magnetic properties are modulated through a mechanically-induced non-uniform strain (e.g. application of ultrasonic energy via a piezoelectric transducer).

In embodiments, magnetic flux leakage is characterized by a single vector magnetometer that is rastered in space to characterize the full magnetic gradient tensor resulting from the applied mechanical excitation.

In embodiments, the flux leakage is characterized through multiple magnetic sensors configured into a magnetic gradiometer that is rastered to characterize the full magnetic gradient tensor.

In embodiments, the flux leakage is characterized through multiple magnetic sensors configured to characterize the full magnetic gradient tensor with no sensor motion relative to the sample under test.

Non-limiting examples of non-uniformities that may be detected through the methods of this disclosure include surface crack, strain, or corrosion; subsurface crack, strain, or corrosion; occluded crack, strain, or corrosion; dissimilar material joints; coatings; alloy precipitates, inclusions, or slag; or any of these nonuniformities either intentionally or unintentionally present in the material.

Not wishing to be bound by a particular theory, different flux leakage paths detected by the methods of the disclosure include magnetostriction of materials resulting in changes in magnetic moment; strain concentration resulting in increased localized heating that change permeability, susceptibility, or saturation magnetization; physical changes in defects that alter internal demagnetization fields to effect changes in permeability or vector of magnetic moment; and changes in reluctance that allow for alterations in flux leakage paths.

In embodiments, the present disclosure also provides a synchronous magnetic field detection system that is capable of detecting and characterizing internal and external flaws in ferrous and non-ferrous materials or components or structures made of these materials. As used herein, "components," or "structures," or "materials" (also referred to as "test samples" or "test items" for example) can be ferrous or non-ferrous objects with simple or complex geometric configurations which may be tubular, cylindrical, cuboid, trapezoid, spheroid, or any 3-dimensional object of any curvilinear and/or rectilinear dimension, including a planar sheet. As used herein, "components" and "structures" and "materials" may function as part of a larger assembly (e.g. piston) or may be functional on its own (e.g. metal pipe).

Figure 1:
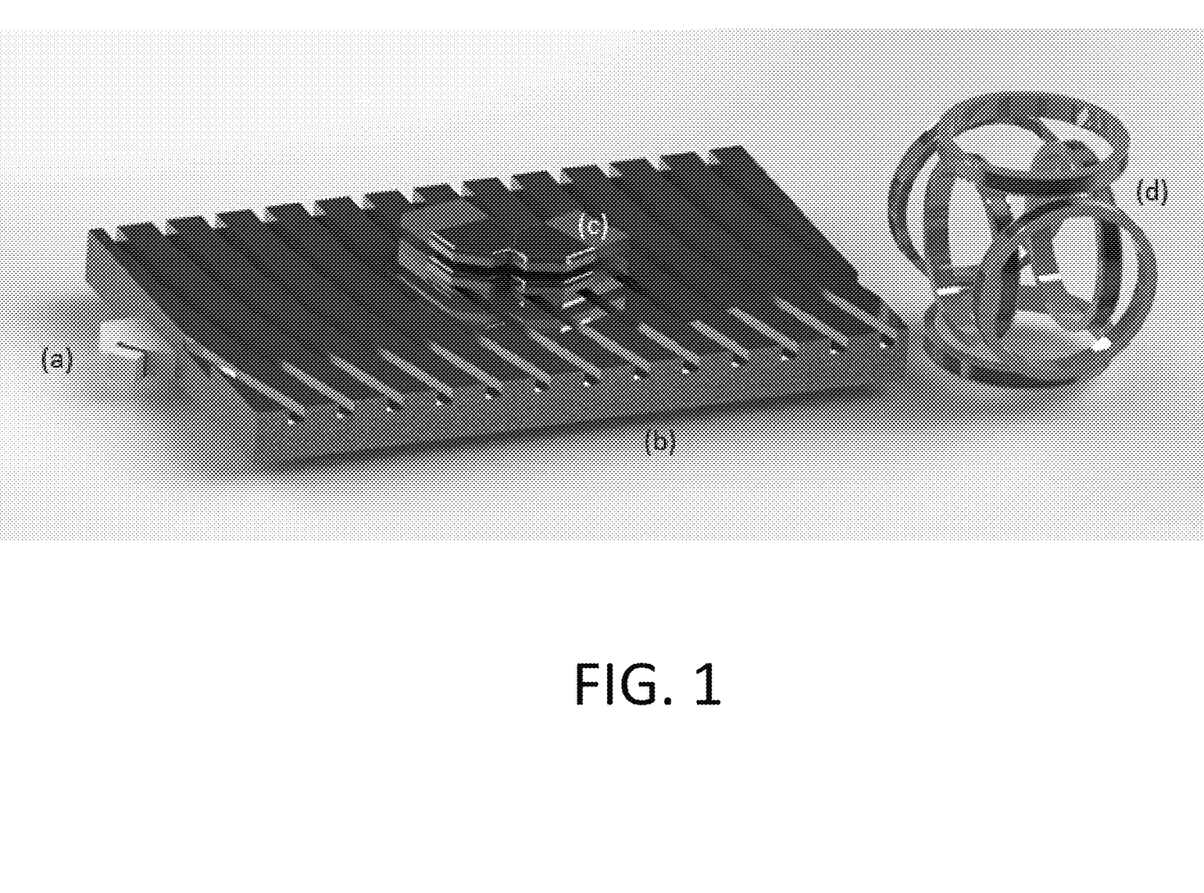
FIG. 1 is a schematic drawing showing representative elements of a synchronous magnetic imaging system according to an embodiment of this disclosure.

The present disclosure provides synchronous magnetic field detection with a periodic mechanical excitation. FIG. 1 shows a particular embodiment of such a system including: (a) an ultrasonic transducer, (b) optionally, a sample material—here, rifled steel with chrome plating, (c) an array of magnetometers, here four magnetometers are shown, and (d) a 3-D Helmholtz coil.

One embodiment of how the system of the disclosure may be implemented would be to launch ultrasonic Rayleigh or Lamb waves into a test item while applying a steady magnetic field laterally through the test area. A preferred magnetic sensor for this application is based on nitrogen vacancies in diamond which can have ultra-high special resolution and B-field resolution at the same time, although any B-field sensor of high enough sensitivity and gradient would suffice. By raster scanning the sensor over the test area, a detailed, 3D mapping of the defect(s) can be generated.

Figure 2A:
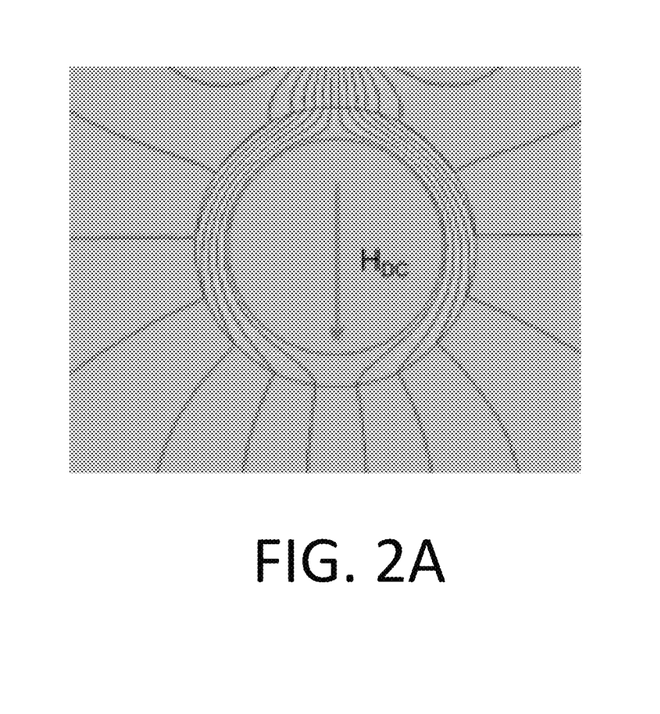
FIGS. 2A and 2B are schematic diagrams showing a front view and a side view of a gun barrel structure with DC magnetic field flux lines according to an embodiment of this disclosure.
Figure 2B:
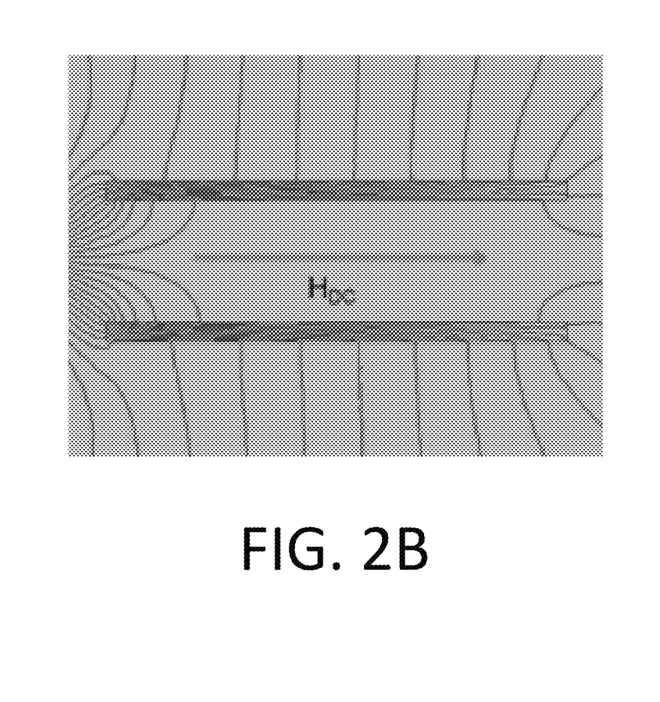

The magnetic flux lines illustrated in FIGS. 2A and 2B demonstrate how magnetic field lines are "channeled" into materials based on their magnetic permeability. Ferrous materials, like steel, have high permeability and tend to absorb more magnetic flux. The denser field lines in the material are evidence of this. A flaw or defect in the material will change the magnetic moment locally, and have an impact on the flux leakage from the structure. The flux leakage is what the magnetometer will detect.

Figure 3:
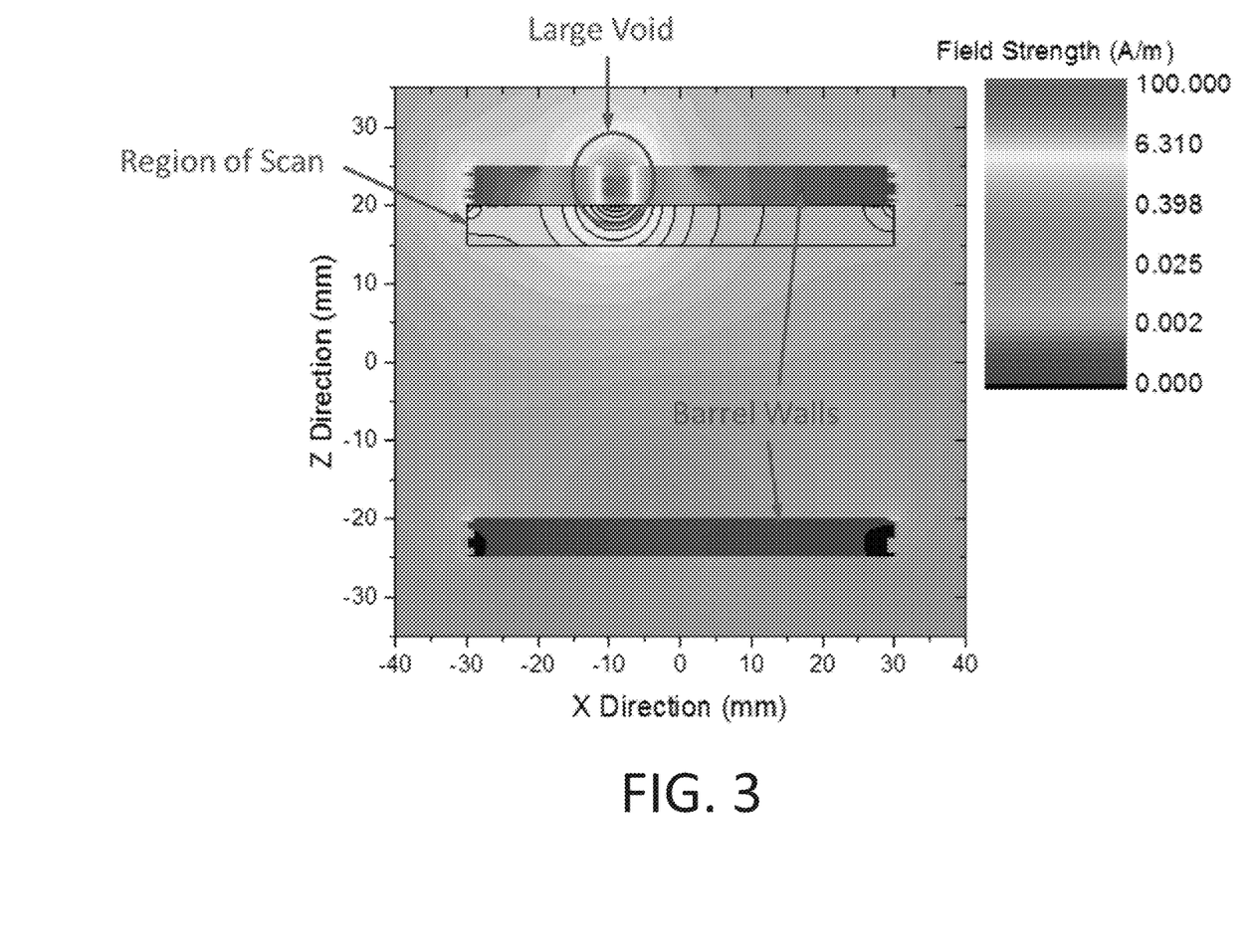
FIG. 3 is a schematic diagram showing flux leakage resulting from a 2 mm internal flaw, with no background magnetic noise.

The flux leakage in FIG. 3 is the result of a large internal flaw. In this scenario, it would be very easy to use a magnetometer to detect the flux leakage and determine that a flaw exists. With a 3-D raster pattern, the size and exact location can also be determined. In reality, there is a large amount of magnetic noise that exists, and this noise is usually orders of magnitude greater than the flux leakage signal associated with an internal flaw.

Figure 4:
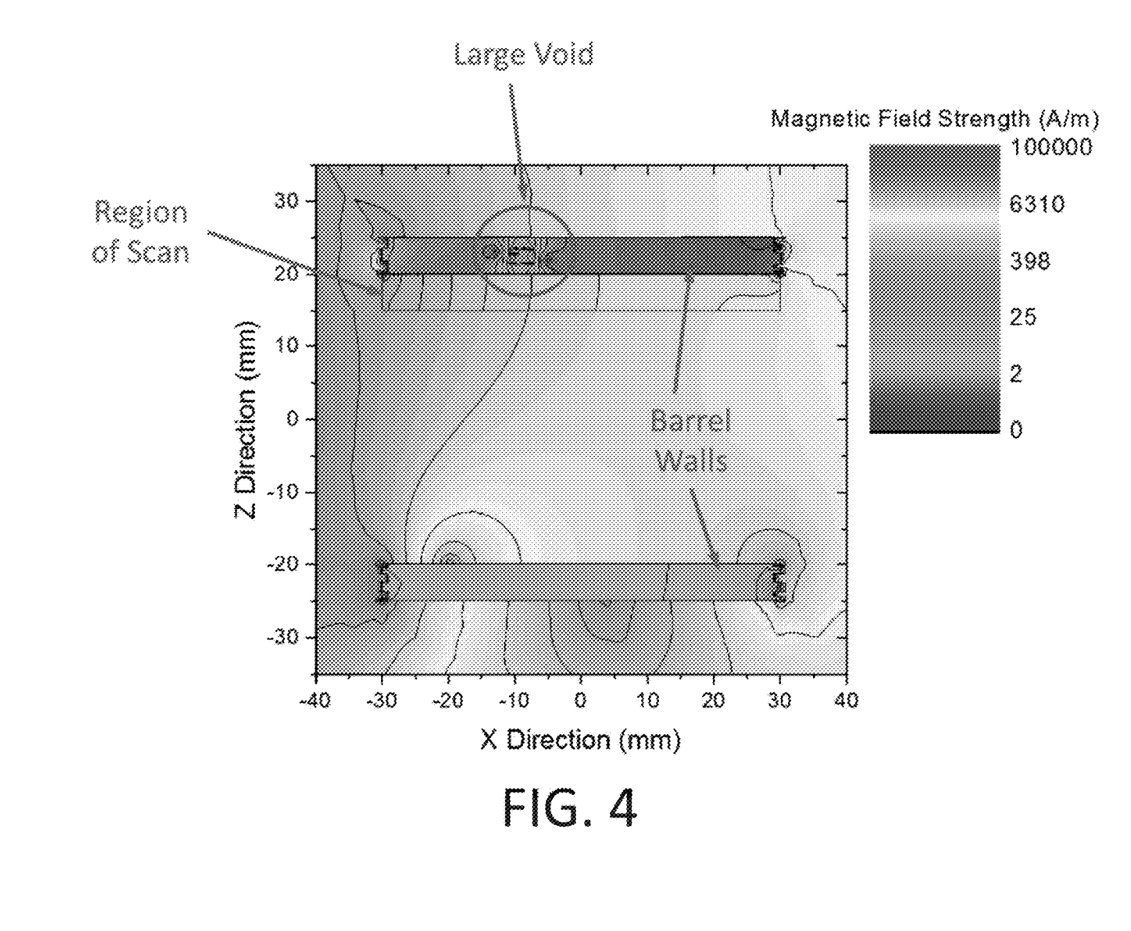
FIG. 4 is a schematic diagram showing a magnetic flux leakage signal with background magnetic noise.

A large amount of magnetic noise has been superimposed onto the structure in FIG. 4, and the flux leakage that was easily detectable in FIG. 3 is no longer discernable. The present disclosure is able to take advantage of magnetostrictive properties to resolve this problem.

Figure 5:
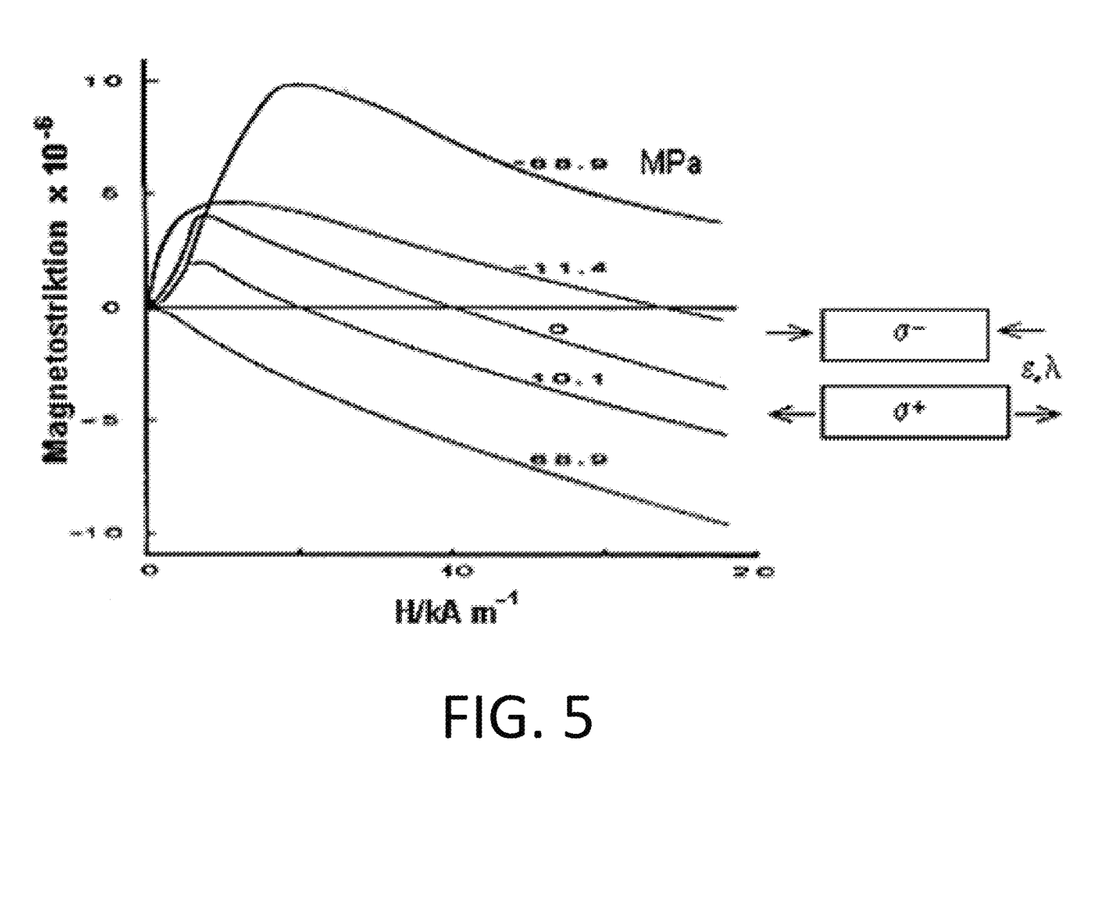
FIG. 5 is a graph showing magnetostriction in structural steel, with the Y axis in units of strain.

Most materials, particularly ferromagnetic materials exhibit a shape change in the presence of an external magnetic field—a phenomenon called magnetostriction. Conversely, the magnetic moment of a ferromagnetic material changes as its strain state changes (Villari effect). Embodiments of the present disclosure use the magnetic field/strain relationship illustrated in FIG. 5 by mechanically exciting the structure with an ultrasonic waveform. As the component cycles between tension and compression, the magnetometer can detect the magnetic field that is synchronous with the excitation frequency. This method allows for background noise to be filtered out so the flaw can be detected.

Figure 6A:
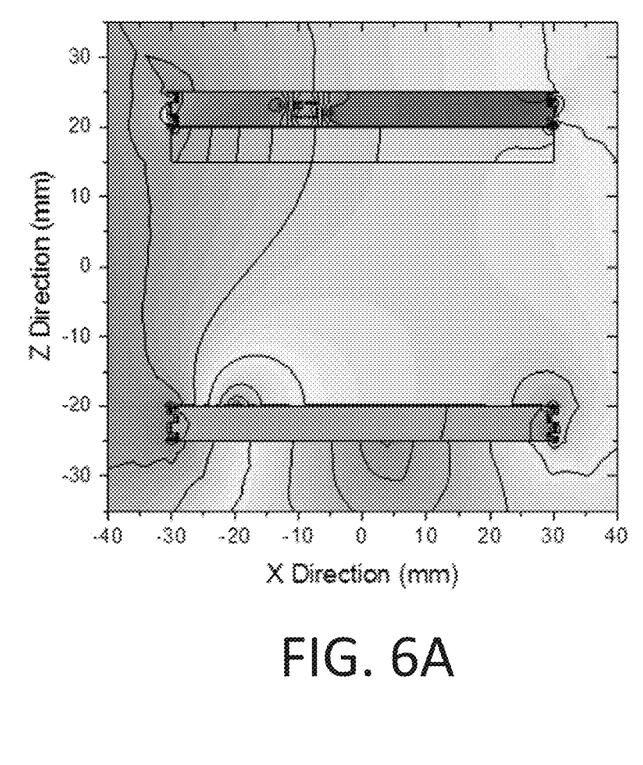
FIG. 6A shows a magnetic field with background noise.
Figure 6B:
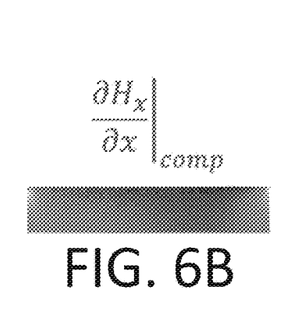
FIG. 6B shows a magnetometer gradient field as the material is in compression.
Figure 6C:
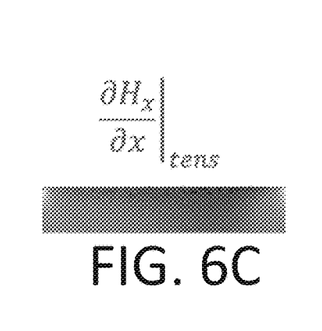
FIG. 6C shows the magnetometer gradient field as the material is in tension.
Figure 6D:
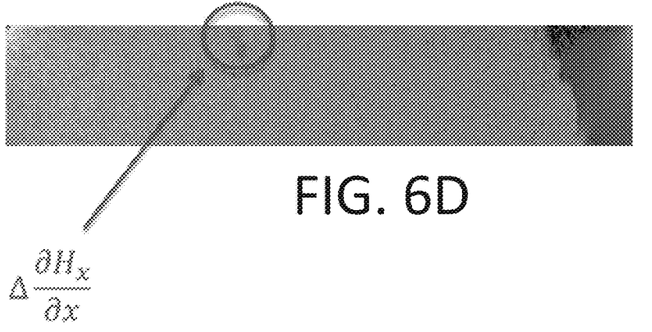
FIG. 6D shows the difference between the scan shown in FIG. 6B and the scan shown in FIG. 6C.

The results in FIGS. 6A-D illustrate the unique capability of flaw detection with magnetometers using synchronous detection. FIG. 6A show a magnetic field with background noise, while FIGS. 6B and 6C show the results of the scan when the material in compression and tension, respectively. Both scans look very similar, almost the same. This is what would be seen if a DC scan was made. The minor differences in magnetic flux are detectable, as seen in FIG. 6D when the individual scans are differentiated. True characterization of the flaw can be made with multiple scans at different x, y and z coordinates.

The methods of this disclosure can be used to create a two dimensional (2D) or 3D image using image processing techniques and algorithms used in Magnetic Resonance Imaging (MRI), such as Fourier transformation which is well known in the art. The image processing algorithms may be executed in a set of computer-executable instructions in storage or memory that may cause a computer processor to create a 2D or 3D image of the flaw. The 2D or 3D image may be captured as a raster-formatted or vector-formatted image file. Additionally, algorithms for determining the spatial coordinates or calculating the 2D area or 3D volume of the flaw may be included in the set of computer executable instructions.

In embodiments, the present disclosure provides a system for detecting a nonuniformity in a material, the system comprising an ultrasound source, optionally a test sample of material, one or more magnetometers, and a magnetic field source, wherein the ultrasound source is configured to induce a cycle of compression and tension in the test sample and the one or more magnetometers are configured to scan the test sample when it is in compression and when it is in tension, wherein the magnetic field source is configured to control the relative magnitude of any flux leakage in the test sample. The system may comprise a single vector magnetometer or an array of magnetometers. In embodiments, the system may further comprise an imaging device and may further comprise a processor and a set of computer-executable instructions configured to obtain a 2D or 3D image of the test sample from multiple scans by the one or more magnetometers.

In embodiments, the magnetometer may be any vector magnetometer, non-limiting examples of which include rotating coil magnetometers, Hall Effect magnetometers, magnetoresistive magnetometers, fluxgate magnetometers, SQUID magnetometers, spin-exchange relaxation-free (SERF) atomic magnetometers, and the like. In embodiments, the magnetometer may be a scalar magnetometer, non-limiting examples of which may include proton precession magnetometers, overhauser effect magnetometers, cesium vapor magnetometers, potassium vapor magnetometers, and the like.

The ultrasonic transducer may be any ultrasonic transducer known in the art including mechanical transducers such as oscillating or rotating transducers or electronic transducers such as sector, curved, linear, or phased arrays. The ultrasound electronic transducer may be based on piezoelectric materials which are known in the art such as piezoelectric crystals or ceramics. The ultrasonic waves may be any type of ultrasonic wave used in the art, including longitudinal waves, transverse waves, Rayleigh waves, Lamb waves, Love waves, Stonely waves, or Sezawa waves. Preferred are Lamb waves which propagate in solid plates and Rayleigh waves which propagate along a surface.

The methods and systems of the present disclosure can be used to detect any non-uniformity, flaw, or defect in any ferrous or non-ferrous material, component or structure, including but not limited to steel sheets, gun barrels, pipes, parts of machinery, parts of motors, components of automobiles, vessels, or aircraft, and the like. The nonuniformity, flaw, or defect may be any size. In embodiments, the nonuniformity, flaw, or defect is preferably less than 100 µM in any dimension and may include a surface crack, strain, or corrosion; subsurface crack, strain, or corrosion; occluded crack, strain, or corrosion; dissimilar material joint; coating; alloy precipitate, inclusion, or slag; or any combination thereof. Further, it is envisioned that the methods of this disclosure will be used as a standard NDT technology for detecting nonuniformities in materials, components, or structures. The methods of this disclosure may be carried out at any location in which suitable equipment such as an ultrasound transducer, magnetometers, or 3-D Helmholtz coil or equivalent equipment is available.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A method of detecting a nonuniformity in a material, component, or structure, the method comprising:
simultaneously:
applying an exterior, DC magnetic bias field to the material, component, or structure, which field is constant over time and spatially uniform;
inducing periodic changes in strain state in the material, component, or structure by periodic excitation at a prescribed or known reference frequency; and
performing synchronous detection of a magnetic flux leakage by:
mixing a measured magnetic signal with the reference frequency, and
low-pass filtering results of the mixing;
thereby measuring only a demodulated magnetic response to the induced periodic changes in strain state, which response consists of the magnetic flux leakage that is synchronous with the induced periodic changes in strain state;
wherein the measured synchronous magnetic flux leakage is sufficient to detect and characterize the nonuniformity in a material, component, or structure.

2. The method of claim 1 further comprising:
applying periodic mechanical force to the material, component, or structure in a manner sufficient to induce changes in the strain state in the material, component, or structure.

3. The method of claim 1 further comprising
exciting the material, component, or structure with periodic waves of ultrasonic energy in a manner sufficient to induce cycles of compression and tension in the material, component, or structure; and
measuring magnetic flux leakage that is synchronous with the cycles of compression and tension.

4. The method of claim 1 further comprising:
applying periodic mechanical force to the material, component, or structure in a manner sufficient to induce changes in the strain state in the material.

5. The method of claim 1 further comprising:
exciting the material, component, or structure with periodic waves of ultrasonic energy in a manner sufficient to induce cycles of compression and tension in the material, component, or structure; and
measuring magnetic flux leakage that is synchronous with the cycles of compression and tension.

6. The method of claim 1 further comprising:
inducing a cycle of tension and compression in the material, component, or structure; and
measuring magnetic flux leakage that is synchronous with the cycles of compression and tension.

7. The method of claim 1, wherein the synchronous magnetic flux leakage has a phase.

8. The method of claim 1, the synchronous magnetic flux leakage has an amplitude and phase.

9. The method of claim 1, wherein the changes in strain state are a mechanically-induced non-uniform strain.

10. The method of claim 9, wherein application of ultrasonic energy produces the mechanically-induced non-uniform strain.

11. The method of claim 9, wherein application of acoustic energy produces the mechanically-induced non-uniform strain.

12. The method of claim 1, wherein the nonuniformity is a surface crack, strain, or corrosion; subsurface crack, strain, or corrosion; occluded crack, strain, or corrosion; dissimilar material joint; coating; alloy precipitate, inclusion, or slag; or any combination thereof.

13. The method of claim 1, wherein multiple scans are performed at different x, y and z coordinates to create a 3D image.

14. The method of claim 1, wherein a Fourier transformation is used to create a 3D image.

15. The method of claim 1, wherein the exterior, DC magnetic bias field is induced by a Helmholtz coil.

16. The method of claim 1, wherein the exterior, DC magnetic bias field is induced by a permanent magnet.

17. The method of claim 16, wherein the exterior, DC magnetic bias field is induced by a Halbach array of permanent magnets.

18. The method of claim 16, wherein the exterior, DC magnetic bias field is induced by an array of permanent magnets.

19. The method of claim 1, wherein the material comprises a ferrous material.

20. The method of claim 1, wherein the material is a non-ferrous material.

21. The method of claim 1, wherein the periodic changes in the strain state in the material, component, or structure are induced by applying periodic mechanical force to the material, component, or structure.

22. The method of claim 1, wherein the periodic changes in the strain state in the material, component, or structure are induced by applying periodic waves of acoustic energy to the material, component, or structure.

23. The method of claim 22, wherein the acoustic energy is ultrasound.

24. The method of claim 1, wherein the periodic changes in the strain state comprise repeated intervals of tension and compression.

25. A method of detecting a nonuniformity in a material, component, or structure, the method comprising:
simultaneously:
applying an exterior, DC magnetic bias field to the material, component, or structure, which field is constant over time and spatially uniform;
periodically changing the magnetic moment of the material, component, or structure through the Villari effect by periodic excitation at a prescribed or known reference frequency; and,
performing synchronous detection of a magnetic flux leakage by:
mixing a measured magnetic signal with the reference frequency, and
low-pass filtering results of the mixing;
thereby measuring only a demodulated magnetic response to the periodic changes in magnetic moment, which response consists of the magnetic flux leakage that is synchronous with the periodic changes in magnetic moment;
wherein the measured synchronous magnetic flux leakage is sufficient to detect and characterize the nonuniformity in a material, component, or structure.

26. A system for detecting a nonuniformity in a material, component, or structure, the system comprising:
an ultrasound source;
one or more magnetometers; and
a magnetic field source;
wherein the ultrasound source is configured to induce cycles of compression and tension at a prescribed or known ultrasound frequency in a test sample and the one or more magnetometers are configured to detect the simultaneous magnetic response of the ultrasound frequency applied to the test sample by providing multiple measures of magnetic flux leakage in the test sample at the same frequency as the ultrasound frequency such that only the magnetic flux leakage that is synchronous with the induced cycles of compression and tension is measured; and
wherein the magnetic field source is configured to control the relative magnitude of any flux leakage in the test sample.

27. The system of claim 26, wherein the ultrasound source comprises an electronic transducer.

28. The system of claim 27, wherein the electronic transducer comprises a piezoelectric material.

29. The system of claim 26, wherein the magnetic field source comprises a Helmholtz coil.

30. The system of claim 26, wherein the magnetic field source comprises a permanent magnet.

31. The system of claim 26, wherein the magnetic field source comprises a set of permanent magnets configured in a Halbach array.

32. The system of claim 26, wherein the magnetic field source comprises a set of permanent magnets configured in a magnetic circuit.

33. The system of claim 26, wherein the magnetic field source comprises a wound-wire solenoid.

34. The system of claim 26, further comprising an imaging device configured for displaying an image of the test sample.

35. The system of claim 26, further comprising a processor and a set of computer-executable instructions configured to obtain a 3D image of the test sample from multiple scans by the one or more magnetometers.

* * * * *